United States Patent [19]

Moriya et al.

[11] Patent Number: 5,368,827
[45] Date of Patent: Nov. 29, 1994

[54] PROCESS FOR THE PRODUCTION OF CRYSTALLINE ADDUCT OF BISPHENOL A AND PHENOL AND APPARATUS THEREFOR

[75] Inventors: Nobuo Moriya, Yokohama; Keiji Shimoda, Machida; Kouji Sakashita, Tokyo; Hiroaki Nishijima, Ebina; Nobuhiro Onda, Hachioji; Takeshi Kouzaki, Yokohama, all of Japan

[73] Assignee: Chiyoda Corporation, Yokohama, Japan

[21] Appl. No.: 967,373

[22] Filed: Oct. 28, 1992

Related U.S. Application Data

[62] Division of Ser. No. 890,103, May 29, 1992, abandoned.

[30] Foreign Application Priority Data

| Jul. 10, 1991 | [JP] | Japan | 3-169557 |
| Oct. 11, 1991 | [JP] | Japan | 3-292211 |
| Oct. 25, 1991 | [JP] | Japan | 3-306520 |
| Oct. 25, 1991 | [JP] | Japan | 3-306521 |

[51] Int. Cl.$^5$ ............................................. C07C 37/20
[52] U.S. Cl. ............................. 422/245.1; 23/295 R; 568/724
[58] Field of Search ................. 422/245, 245.1; 23/295 R; 568/724, 727

[56] References Cited

U.S. PATENT DOCUMENTS

| 2,683,178 | 7/1954 | Findlay | 422/245 |
| 4,209,646 | 6/1980 | Gac et al. | 568/724 |
| 4,950,804 | 8/1990 | Iimuro et al. | 568/727 |
| 4,950,805 | 8/1990 | Iimuro et al. | 568/724 |
| 4,950,806 | 8/1990 | Iimuro et al. | 568/727 |
| 4,954,661 | 9/1990 | Iimuro et al. | 568/727 |

FOREIGN PATENT DOCUMENTS

| 687780 | 6/1964 | Canada | 568/724 |
| 0330146 | 8/1989 | European Pat. Off. . | |
| 0332878 | 9/1989 | European Pat. Off. . | |
| 2289476 | 5/1986 | France . | |
| 1180038 | 9/1985 | U.S.S.R. | 422/245 |

OTHER PUBLICATIONS

CEP, May 1986, "Industrial Crystallization For Ultrapure Products".
European Search Report dated Sep. 16, 1993.

Primary Examiner—Robert Kunemund
Attorney, Agent, or Firm—Armstrong, Westerman, Hattori, McLeland & Naughton

[57] ABSTRACT

High purity, crystalline adduct of bisphenol A and phenol is produced multi-stage crystallization of a phenolic slurry of bisphenol A with a crystal separation and washing step being interposed between each of the two stages. Each of the crystallization stage includes a series of crystallization towers operated at decreasing temperatures. The crystallization of the slurry is performed by continuously discharging a portion of the slurry from each of the crystallization towers, introducing the discharged slurry into one or more coolers and then recycling the cooled slurry to the tower. Another portion of the slurry in each crystallization slurry is continuously discharged, heated for dissolving fine crystals of the adduct and then recycled to the crystallization tower so that large crystals are grown in each of the crystallization steps. An apparatus having a plurality of coolers and suitable for effecting the above crystallization is also disclosed.

1 Claim, 5 Drawing Sheets

PROCESS FOR THE PRODUCTION OF CRYSTALLINE ADDUCT OF BISPHENOL A AND PHENOL AND APPARATUS THEREFOR

This is a division, of application Ser. No. 890,103 filed May 29, 1992, now abandoned.

This invention relates to a process for the production of a crystalline adduct of bisphenol A and phenol and to an apparatus suitable for carrying out the process.

One well known process for the production of bisphenol A (2,2-bis(4'-hydroxyphenyl)propane) includes reacting acetone with a stoichiometrically excess amount of phenol in the presence of an acid catalyst. With respect to the recovery of bisphenol A from the reaction product, a method is known in which the reaction product is cooled for the crystallization of a bisphenol A/phenol adduct and the resulting adduct is subsequently decomposed into bisphenol A and phenol (U.S. Pat. No. 3,936,507).

Since the purity and hue of bisphenol A recovered from a bisphenol A/phenol adduct depend largely upon the purity and hue of the adduct, it is highly desired to produce colorless, high purity crystals of the adduct. To attain this purpose, a method is proposed in which a solution of bisphenol A in phenol is subjected to a series of crystallization stages each of which is followed by separation of crystals and dissolution of the separated crystals. With this method, it is possible to improve the purity of the adduct by increasing the number and/or the size of the crystallization towers. However, since the number and size of the adduct separators and their associated dissolving vessels are also increased with the increase of crystallization towers, the whole apparatus becomes undesirably large, complicated and inefficient.

The crystallization of the adduct of bisphenol A and phenol is generally performed by feeding a solution of bisphenol A in phenol to a crystallization tower and cooling the solution in the tower to form a slurry of the adduct. The cooling is performed by continuously discharging part of the slurry from the tower, introducing the discharged slurry into a cooler and recycling the cooled slurry to the tower. This cooling method has a problem because it is difficult to control the size of the crystals of the adduct and because fine crystals of the adduct are apt to be produced. Because of their large surface area, the fine crystals of the adduct have a tendency to adsorb impurities.

The present invention has been made with the foregoing problems of the conventional method in view and provides a process and an apparatus which can efficiently produce a high quality bisphenol A/phenol adduct having a low content of impurities and excellent hue (color characteristics).

In accordance with one aspect of the present invention, there is provided a process for the production of a crystalline adduct of bisphenol A and phenol, comprising the steps of:

feeding a first solution of bisphenol A dissolved in phenol to a first crystallization zone and cooling same at a first temperature sufficient to crystallize an adduct of bisphenol A and phenol and to obtain a first slurry containing crystals of the adduct;

introducing the first slurry into a second crystallization zone and cooling same at a second temperature which is lower than the first temperature to permit the crystals of the adduct to grow and to obtain a second slurry containing the grown crystals;

introducing the second slurry into a solid liquid separator to separate the second slurry into a solid phase containing the grown crystals and a liquid phase containing phenol;

dissolving the solid phase in purified phenol having a higher purity than the liquid phase to obtain a second solution;

feeding the second solution to a third crystallization zone and cooling same at a third temperature sufficient to crystallize an adduct of bisphenol A and phenol and to obtain a third slurry containing crystals of the adduct;

introducing the third slurry into a fourth crystallization zone and cooling same at a fourth temperature which is lower than the third temperature to permit the crystals of the adduct to grow and to obtain a fourth slurry containing the grown crystals; and recovering the grown crystals from the fourth slurry.

In another aspect, the present invention provides a process for the production of a crystalline adduct of bisphenol A and phenol, comprising the steps of:

providing two or more, first to n-th crystallization zones connected in series and each having an outer tubular housing and an inner tubular member defining therein an inner passage and coaxially disposed within said outer tubular housing to define an outer passage therebetween, said inner passage being in fluid communication with said outer passage only at an upper portion of said inner passage;

crystallizing an adduct of bisphenol A and phenol in each of said first to n-th crystallization zones to form a slurry;

discharging the slurry from the bottom of the inner passage of each of said first to n-th crystallization zones;

cooling a portion of the slurry discharged from each of said two or more crystallization zones and recycling the cooled slurry to the corresponding crystallization zone so that the slurry in each of said first to n-th crystallization zones is cooled such that the temperature of the slurry in one crystallization zone is lower than that in the adjacent crystallization zone located upstream of said one crystallization zone;

heating another portion of the slurry discharged from said n-th crystallization zone to dissolve fine crystals contained therein and recycling said heated slurry to said n-th crystallization zone;

admixing a solution of bisphenol A dissolved in phenol with said cooled slurry to be recycled to said first crystallization zone, feeding the resulting admixture to the outer passage of the first crystallization zone and passing same to the inner passage to effect the crystallization of the adduct of bisphenol A and phenol;

mixing part of the slurry discharged from each of said first to (n−1)th crystallization zones with the cooled slurry to be recycled to that crystallization zone located immediately downstream thereof, feeding the resulting mixture to the outer passage of that crystallization zone and passing same to the inner passage of that crystallization zone to effect the crystallization of the adduct of bisphenol A and phenol; and recovering a further portion of the slurry discharged from said n-th crystallization zone.

In a further aspect, the present invention provides a process for the production of a crystalline adduct of bisphenol A and phenol, comprising the steps of:

providing a crystallization zone having an outer cylindrical housing and an inner cylindrical member defining therein an inner passage and coaxially disposed within the outer cylindrical housing to define an annular, outer passage therebetween, the inner passage being in fluid communication with the outer passage only at an upper portion of the inner passage;

feeding a solution of bisphenol A dissolved in phenol to the outer passage of the first crystallization zone and passing same to the inner passage while cooling same crystallize an adduct of bisphenol A and phenol and to obtain a slurry containing crystals of the adduct;

discharging the slurry from the bottom of the inner passage of the crystallization zone;

cooling a first portion of the slurry discharged from the crystallization zone and recycling the cooled slurry to the crystallization zone so that the slurry in the crystallization zone is cooled;

heating a second portion of the slurry discharged from the crystallization zone to dissolve fine crystals contained therein and recycling the heated slurry to the crystallization zone; and recovering the crystals from the slurry discharged from the crystallization zone, each of the solution, the cooled slurry and the heated slurry being fed to the outer passage of the crystallization zone such that the slurry in the outer passage forms a vortex flow.

In yet a further aspect, the present invention provides a process for the production of a crystalline adduct of bisphenol A and phenol, comprising the steps of:

providing a crystallization zone and a plurality of cooling zones connected in parallel with each other and each having a cooling surface adapted to cool a liquid upon contact therewith;

feeding a solution of bisphenol A dissolved in phenol to the crystallization zone and cooling same to crystallize an adduct of bisphenol A and phenol and to obtain a slurry containing crystals of the adduct;

discharging the slurry from the crystallization zone;

introducing a portion of the slurry discharged from the crystallization zone to all of the cooling zones except one cooling zone whose cooling surface bears deposits of crystals of the adduct to cool the slurry introduced thereinto with the simultaneous formation of crystals of the adduct part of which deposit on the cooling surfaces thereof;

recycling the cooled slurry to the crystallization zone so that the slurry in the crystallization zone is cooled;

recovering the crystals from the slurry discharged from the crystallization zone; and removing the deposits from the cooling surface of the one cooling zone.

In yet a further aspect, the present invention provides a process for the production of a crystalline adduct of bisphenol A and phenol, comprising:

(A) a first stage including the steps of:
(A-a) feeding a solution of bisphenol A dissolved in phenol to a crystallization zone and cooling same to crystallize an adduct of bisphenol A and phenol and to obtain a slurry containing crystals of the adduct, and (A-b) discharging the slurry from the crystallization zone and introducing same into a solid-liquid separating zone to separate the slurry into a solid phase containing crystals of the adduct and a liquid phase containing phenol; and (B) one or more, second to n-th stages following said first stage and each including the steps of:
(B-a) dissolving the solid phase obtained in the immediately preceding stage into solvent phenol to obtain a solution, (B-b) feeding the solution obtained in step (B-a) to a crystallization zone and cooling same to crystallize an adduct of bisphenol A and phenol and to obtain a slurry containing crystals of the adduct, and (B-c) discharging the slurry obtained in step (B-b) from the crystallization zone and introducing same into a solid-liquid separating zone to separate the slurry into a solid phase containing crystals of the adduct and a liquid phase containing phenol, the process further comprising the steps of:

washing the solid phase obtained in the n-th stage with purified phenol to obtain a washed solid product and used phenol, recovering the washed solid product, recycling at least one of a first part of the used phenol and a first part of the liquid phase obtained in the n-th stage to step (B-a) of the (n−1)th stage as at least part of the solvent phenol, washing the solid phase obtained in the (n−1)th stage with at least one of a second part of the used phenol and a second part of the liquid phase obtained in the n-th stage, and controlling the purity of the solvent phenol used in each of the second to n-th stages so that the content of impurities in the solvent phenol used in one stage of the second to n-th stages is greater than that of the stage immediately following the one stage.

In yet a further aspect, the present invention provides a process for the production of a crystalline adduct of bisphenol A and phenol, comprising:

cooling a solution of bisphenol A dissolved in phenol to crystallize an adduct of bisphenol A and phenol and to obtain a slurry containing crystals of the adduct, and filtering the slurry to separate the crystals such that the separated crystals contain less than 20% by weight of crystals with a particle diameter of 100 μm or less.

In accordance with a further aspect of the present invention, there is provided an apparatus for production of a crystalline adduct of bisphenol A and phenol, comprising:

a crystallization tower containing a slurry of crystals of an adduct of bisphenol A and phenol dispersed in phenol and having a recycling port and a discharge port;

a plurality of coolers each having an inlet port and an outlet port;

first conduit means extending between the discharge port of the crystallization tower and the inlet port of each of the coolers;

second conduit means extending between the recycling port of the crystallization tower and the outlet port of each of the coolers; and pump means operable to continuously discharge part of the slurry from the crystallization tower, to pass the discharged slurry through the plurality of coolers with selected one of the plurality of coolers being prevented from being fed with the discharged slurry and to return the discharged slurry after the passage of the coolers to the recycling port, whereby the slurry within the crystallization tower is cooled with the recycled slurry which has been passed through the coolers to cause the crystals to grow.

The present invention also provides a crystallization device, comprising:

a first crystallization tower for containing a slurry of crystals of an adduct of bisphenol A and phenol dispersed in phenol and having a recycling port, a discharge port and a feed port;

a feed conduit connected to the intermediate feed port of the first crystallization tower for feeding a liquid mixture of bisphenol A and phenol;

a second crystallization tower containing a slurry of crystals of an adduct of bisphenol A and phenol dispersed in phenol and having a recycling port, a discharge port and a feed port;

a first group of two or more coolers each having inlet and outlet ports;

a second group of two or more coolers each having inlet and outlet ports;

a common cooler having inlet and outlet ports;

feed conduit means extending between the discharge port of the first crystallization tower and the feed port of the second crystallization tower and having feed pump means for feeding a portion of the slurry in the first crystallization tower into the second crystallization tower through the feed conduit means;

first introduction conduit means extending between the discharge port of the first crystallization tower and the inlet port of each of the coolers of the first group;

first recycling conduit means extending between the recycling port of the first crystallization tower and the outlet port of each of the coolers of the first group;

second introduction conduit means extending between the discharge port of the second crystallization tower and the inlet port of each of the coolers of the second group;

second recycling conduit means extending between the recycling port of the second crystallization tower and the outlet port of each of the coolers of the second group;

a recovery conduit in communication with the discharge port of the second crystallization port for discharging part of the slurry from the second crystallization tower therethrough for recovery;

common introduction conduit means for communicating the inlet port of the common cooler with the discharge port of each of the first and second crystallization towers;

common recycling conduit means for communicating the outlet port of the common cooler with the recycling port of each of the first and second crystallization towers;

first pump means operable to continuously discharge part of the slurry from the first crystallization tower, to pass the discharged slurry through the first group of coolers and to return the discharged slurry after the passage of the coolers to the recycling port of the first crystallization tower;

second pump means operable to continuously discharge part of the slurry from the second crystallization tower, to pass the discharged slurry through the second group of coolers and to return the discharged slurry after the passage of the coolers to the recycling port of the second crystallization tower;

third pump means operable to continuously discharge part of the slurry from the first or second crystallization tower, to pass the discharged slurry through the common cooler and to return the discharged slurry after the passage of the common cooler to the recycling port of the first or second crystallization tower; and controlling means to control the operations of the first, second and third pump means so that selected one of the common cooler and first and second groups of cooler is prevented from being fed with the discharged slurry, whereby the slurry within each of the first and second crystallization towers is cooled with the recycled slurry which has been passed through the the coolers to cause the crystals in each of the first and second crystallization towers to grow.

The present invention will now be described in detail below with reference to the accompanying drawings, in which:

In the following descriptions, bisphenol A is referred to as BPA for brevity.

FIRST EMBODIMENT

Figure 1:
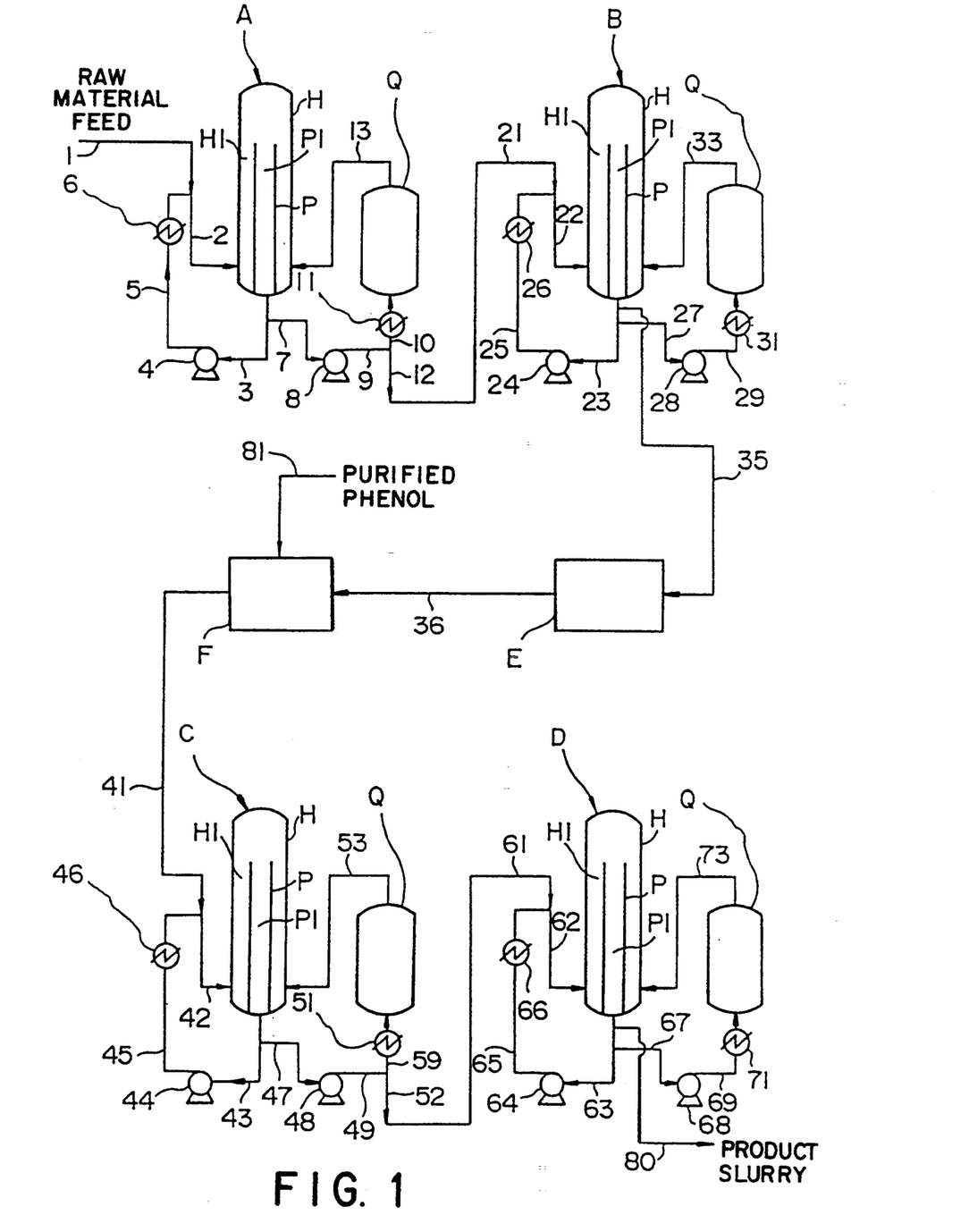
FIGS. 1-5 are flow diagrams of apparatuses suitable for carrying out preferred embodiments of the process according to the present invention.

Referring first to FIG. 1, the symbols A–D designate first through fourth crystallization zones, generally crystallization towers, respectively. Each of the crystallization towers A–D preferably has an outer tubular housing H and an inner tubular member P defining therein an inner passage P1 and coaxially disposed within the outer tubular housing H to define an outer passage H1 therebetween. The inner passage P1 is in fluid communication with the outer passage H1 only at an upper portion thereof. The first and second crystallization towers A and B are connected in series and form a first crystallization stage while the third and fourth crystallization towers C and D are connected in series and form a second crystallization stage. Each of the towers A–D has a dissolution tank Q.

A raw material feed of a solution of BPA dissolved in phenol is continuously introduced through lines 1 and 2 to a lower part of the outer passage H1 of the first crystallization tower A and is directed upward through the outer passage H1. The solution is then allow to enter the inner passage P1 from the open topped end of the inside tubular member P and is directed downward therethrough. During the passage of the feed solution through the outer and inner passages H1 and P1 of the tower A, the solution is cooled to a predetermined temperature so that BPA is crystallized as an adduct of phenol to form a slurry containing seed crystals of the adduct.

For the purpose of effecting the cooling in the first crystallization tower A, a portion of the slurry is discharged from the bottom of the inner tubular member P, introduced into a cooler 6 through a line 3, a pump 4 and a line 5 and then recycled to the tower A through the line 2.

Another portion of the slurry is discharged from the tower A, introduced into a dissolution vessel Q through a line 7, a pump 8, lines 9 and 10 and a heater 11, and then recycled to a lower portion of the outer passage H1 of the crystallization tower A through a line 13. By this, fine crystals contained in the discharged slurry are dissolved and, hence, the proportion of large crystals of the adduct contained in the slurry within the tower A is increased. Fine crystals of the adduct formed in the tower A have a large surface area and are apt to adsorb impurities which account for the coloring of the adduct. By the decrease of the amount of such fine crystals, therefore, it is possible to obtain seed crystals with good hue. Preferably, the content of crystals of the adduct having a particle size of 100 $\mu$m or less is controlled to not greater than 30% by weight, more preferably not greater than 20% by weight, based on the total weight of the adduct crystals recovered from the first crystallization tower A.

The raw material feed introduced through the line 1 into the first crystallization tower A generally contains BPA in an amount of 7–50% by weight, preferably 10–30% by weight, and by-products such as isomers of BPA and trisphenol in an amount of less than 8% by weight.

The temperature of the raw material feed is generally higher by 1°–20° C. than the saturation temperature of the adduct. The crystallization in the tower A is performed at a temperature in the range of 45°–70° C., preferably 48°–57° C. The slurry is cooled in the cooler 6 such that the slurry leaving the cooler 6 has a temperature lower by 10° C. or less, preferably by 5° C. or less, than that of the slurry prior to its passage through the cooler 6. The residence time of the phenol solution of BPA in the first crystallization tower A is generally 0.5–10 hours, preferably 0.5–5 hours. The slurry is heated in the heater 11 such that the slurry leaving the heater 11 has a temperature higher by 0.5°–5° C. than that of the slurry prior to its passage through the heater 11. The residence time of the slurry in the dissolution tank Q is generally 3–15 minutes. In the tank Q, crystals of the adduct having particle size of 100 $\mu$m or less are completely dissolved.

A further portion of the slurry is discharged from the bottom of the inner tubular member P of the first crystallization tower A and is introduced through the line 7, the pump 8 and lines 9, 12, 21 and 22 into a lower portion of the outer passage H1 of the second crystallization tower B. The slurry thus fed to the second crystallization tower B is treated in a manner similar to that of the first crystallization tower A to permit the crystals of the adduct to grow.

The crystallization in the tower B is performed at a temperature in the range of 45°–70° C. and lower by generally 3°–10° C. than the crystallization temperature in the tower A. The slurry is cooled in a cooler 26 such that the slurry leaving the cooler 26 has a temperature lower by 10° C. or less, preferably by 5° C. or less, than that of tile slurry prior to its passage through the cooler 26. The slurry is heated in a heater 31 such that the slurry leaving the heater 31 has a temperature higher by 0.5°–5° C. than that of the slurry prior to its passage through the heater 31. In a dissolution tank Q connected to the second crystallization tower B, crystals of the adduct having particle size of 100 $\mu$m or less are completely dissolved. The concentration of the adduct in the slurry discharged from the bottom of the inner tubular member P1 of the second crystallization tower B is generally 35% by weight or less, preferably 25% by weight or less. The content of crystals of the adduct having a particle size of 100 $\mu$m or less is preferably controlled to not greater than 30% by weight, more preferably not greater than 20% by weight, based on the total weight of the adduct crystals recovered from the first crystallization tower A.

A portion of the slurry is discharged from the second crystallization tower B and is fed through a line 35 to a solid liquid separator E, generally a filtration device or a centrifuge, to separate the slurry into crystals of the adduct and a mother liquor containing phenol. The crystals thus separated are fed through a line 36 to a dissolution zone F, such as a vessel equipped with a stirrer and/or heater, where the crystals are dissolved in purified phenol supplied through a line 81 to obtain a phenol solution of BPA having a BPA concentration of generally 7–50% by weight, preferably 10–30% by weight. The dissolution of the adduct crystals is preferably performed at a temperature of 70°–160° C., more preferably 80°–100° C. The purified phenol to be used as a solvent has a higher purity as compared with that of the mother liquor.

Any purified phenol may be used as long as it is substantially free of impurities which would account for the coloring of BPA. Since generally available phenol contains an impurity, such as benzofuran and derivatives thereof and aromatic aldehydes and derivatives thereof, which is responsible for the coloring of BPA, it is essential to remove or reduce such an impurity prior to the use thereof for the dissolution of the adduct crystals.

Preferably used is purified phenol obtained by a method including the steps of (a) providing raw material phenol which contains impurity, such as mentioned immediately above, capable of forming a high boiling point material having a boiling point of higher than 185° C. when heated at a temperature higher than the melting point of phenol, (b) contacting the raw material phenol with a strong-acid ion exchange resin at such a temperature as to convert at least part of the impurity into the high boiling point material and to obtain treated phenol, and (c) distilling the treated phenol at a temperature of 185° C. or less to separate phenol as distillate from the high boiling point material.

The raw material phenol is preferably selected from (A) phenol for industrial use, (B) phenol separated from a reaction product of phenol and acetone, (C) phenol separated from a crystallization product of BPA-containing phenol and (D) phenol used for washing a crystalline adduct. The raw material phenol preferably has a purity of at least 95% by weight, more preferably at least 97% by weight.

Commercially available phenol of an industrial use grade with a purity of 95% or more may be suitably used as above phenol (A).

After completion of the reaction of acetone with phenol, the product is generally subjected to a separation treatment for removing a part of unreacted phenol therefrom. The phenol thus recovered may be used as raw material phenol (B).

The product obtained by reaction of acetone with phenol is treated to form a crystalline adduct of BPA and phenol. Crystallization is generally performed at a temperature of about 41°–80° C. After crystallization, the mixture is subjected to solid-liquid separation to separate the mixture into a crystalline adduct and a mother liquor. Generally, such crystallization and solid-liquid separation is repeated several times. Thus, phenol is recovered as a mother liquor in each of the solid-liquid separation stages. Such recovered phenol may be used as raw material phenol (C). The phenol recovered in the initial crystallization and separation step is preferably used.

Phenol which has been used for washing the crystalline adduct is recovered. Such phenol may be suitably reused, after being purified, for washing the adduct. Thus, phenol recovered in the washing step may be used as raw material phenol (D). The raw material phenol (B)–(D) may be one recovered in the process shown in FIG. 1 or in any other BPA/phenol adduct production processes.

The purification of above raw material phenol (A)–(D) is performed as follows. The raw material phenol is first contacted with a strong-acid ion exchange resin, generally a sulfonic acid-type ion exchange resin, such as a sulfonated styrene-divinylbenzene copolymer, a sulfonated, cross-linked styrene polymer, a phenol-formaldehyde-sulfonic acid resin or a benzene-formaldehyde-sulfonic acid resin. The ion exchange resin has a cross-linked structure and is insoluble in water. Known sulfonic acid-type ion exchange resins are of a gel-type or a microporous-type. While both types of the ion exchange resins may be used for the purpose of the present invention, the use of a gel-type ion exchange resin is advisable because the activity thereof remains unchanged during use. The gel-type ion exchange resin generally has a degree of cross-linking (the amount of the cross-linking agent contained in the resin) of 10% by weight or less, preferably 5% by weight or less. Illustrative of suitable commercially available, gel-type ion exchange reins are Amberlite, Amberlyst (both manufactured by Rohm & Haas Company) and DIAION (manufactured by Mitsubishi Kasei Inc.).

The contact of the raw material phenol with the ion exchange resin may be carried out by passing the raw material phenol through a fixed layer of the ion exchange packed in a tower or by stirring a mixture of the phenol and the ion exchange resin in a vessel. The contact is generally performed at 45°–150° C., preferably 50°–100° C. for 5–200 minutes, preferably 15–60 minutes. It is preferred that the raw material phenol have a water content of 0.5% by weight or less, more preferably 0.1% by weight or less, for reasons of improved impurity removing effect. The removal of moisture from the raw material phenol may be effected by azeotropic distillation using a suitable known azeotrope agent.

By the contact with the ion exchange resin, the impurities such as benzofuran and derivatives thereof and aromatic aldehydes and derivatives thereof contained in the raw material phenol are converted into high boiling point substances with the ion exchange resin serving as a catalyst.

The raw material phenol which has been treated with the strong-acid ion exchange resin is then distilled to obtain purified phenol as a distillate, with high boiling point impurities formed in the previous treatment with the ion exchange resin being separated as distillation residues.

The distillation is performed under conditions so that the high boiling point impurities are not contained in the distillate. To achieve this purpose, it is preferable to perform the distillation at a temperature of 185° C. or less. At a temperature higher than 185° C., the high boiling point impurities tend to be decomposed and to contaminate the distillate. While the distillation may be carried out at army desired pressure, a reduced pressure of 50–600 Torr is preferably used. The thus obtained purified phenol has a an APHA color of 10 , or less so that it does not adversely affect the hue of BPA when used for washing the adduct of BPA and phenol.

Referring still to FIG. 1, the phenol solution of BPA thus prepared in the dissolution vessel F is introduced through a line 41 into a lower portion of the outer passage H1 of the third crystallization tower C which constitutes part of the second crystallization stage. The slurry thus fed to the third crystallization tower C is treated in a manner similar to that of the first crystallization tower A to form a slurry containing crystals of the adduct.

The crystallization in the tower C is performed at a temperature in the range of 45°–70° C. and equal to or higher by generally 10° C. or less than the crystallization temperature in the tower A. A portion of the slurry is discharged from the bottom of the tower C and cooled in a cooler 46 such that the slurry leaving the cooler 46 has a temperature lower by 10° C. or less, preferably by 5° C. or less, than that of the slurry prior to its passage through the cooler 46. Another portion of the slurry is discharged from the tower C and heated in a heater 51 such that the slurry leaving the heater 51 has a temperature higher by 0.5°–5° C. than that of the slurry prior to its passage through the heater 31. In a dissolution tank Q connected to the third crystallization tower C, crystals of the adduct having particle size of 100 $\mu$m or less are completely dissolved.

A further portion of the slurry is discharged from the bottom of the inner tubular member P of the third crystallization tower C and is introduced through a line 47, a pump 48 and lines 49, 52 and 61 into a lower portion of the outer passage H1 of the fourth crystallization tower D. The slurry thus fed to the fourth crystallization tower D is treated in a manner similar to that of the first crystallization tower B to permit the crystals of the adduct to grow.

The crystallization in the fourth tower D is performed at a temperature which is in the range of 45°–70° C., which is equal to or lower by generally 10° C. or less than the crystallization temperature in the third tower C and which is equal to or higher by 10° C. or less than the crystallization temperature of the second tower B. A portion of the slurry is cooled in a cooler 66 and the cooled slurry is recycled to the tower D to maintain the temperature in the tower D in the above-described range. Another portion of the slurry is heated in a heater 71 such that the slurry leaving the heater 71 has a temperature higher by 0.5°–5° C. than that of the slurry prior to its passage through the heater 31. In a dissolution tank Q connected to the fourth crystallization tower D, crystals of the adduct having particle size of 100 $\mu$m or less are completely dissolved. The concentration of the adduct in the slurry discharged from the bottom of the inner tubular member P1 of the fourth crystallization tower D is generally 35% by weight or less, preferably 25% by weight or less. The content of crystals of the adduct having a particle size of 100 μm or less is preferably controlled to not greater than 30% by weight, more preferably not greater than 20% by weight, based on the total weight of the adduct crystals recovered from the fourth crystallization tower D.

A further portion of the slurry is discharged from the fourth tower D and is recovered through a line 80. The slurry is then fed to a solid-liquid separator (not shown) to obtain high purity grown crystals of the adduct having APHA color of 15 or less. The crystalline adduct is then decomposed to obtain BPA with a high purity and a good hue.

SECOND EMBODIMENT

Figure 2:
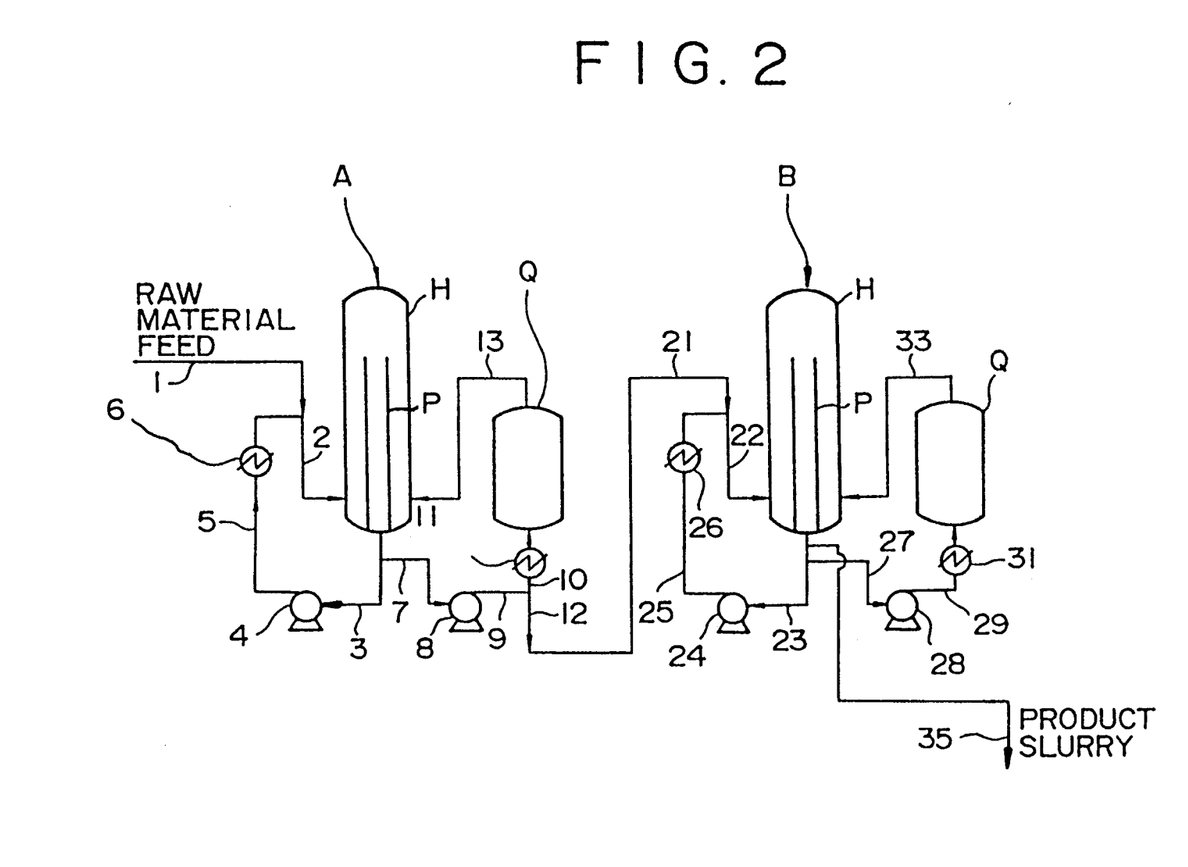

Another embodiment according to the present invention is illustrated in FIG. 2 in which the same reference numerals as in FIG. 1 designate similar component parts.

The apparatus shown in FIG. 2 has two, first and second crystallization towers A and B each of which is composed of an outer tubular, preferably cylindrical housing H and an inner tubular, preferably cylindrical member P defining therein an inner passage P1 and coaxially disposed within the outer tubular housing H to define an outer passage H1 therebetween. The inner passage P1 is in fluid communication with the outer passage H1 only at an upper portion thereof. Each of the towers A and B has a dissolution tank Q.

In each of the crystallization towers A and B, a slurry containing crystals of BPA/phenol adduct dispersed in phenol is contained. Part of the slurry is continuously discharged from the bottom of the inner tubular member P of the tower A (or B) and a portion of the discharged slurry is introduced into a cooler 6 (26) through a line 3 (23), a pump 4 (24) and a line 5 (25). The cooled slurry is then recycled to the tower A (B) through the line 2 (22) for the purpose of effecting the cooling in the crystallization tower A (B).

Another portion of the slurry discharged from the tower A (or B) is introduced into a dissolution vessel Q through a line 7 (27), a pump 8 (28), lines 9 and 10 (line 29) and a heater 11 (31), and then recycled to a lower portion of the outer passage H1 of the crystallization tower A (B) through a line 13 (33). By this, fine crystals contained in the discharged slurry are dissolved and, hence, the proportion of large crystals of the adduct contained in the slurry within each of the towers A and B is increased. Fine crystals of the adduct have a large surface area and are apt to adsorb impurities which account for the coloring of the adduct. By the decrease of the amount of such fine crystals, therefore, it is possible to obtain seed crystals with good hue. Preferably, the content of crystals of the adduct having a particle size of 100 μm or less is controlled to not greater than 30% by weight, more preferably not greater than 20% by weight, based on the total weight of the adduct crystals recovered from the corresponding crystallization tower.

It is preferred that the slurry from the lines 2 and 13 (22 and 33) be introduced into the tower A (B) in such a manner that an upwardly flowing vortex is established in the outer passage H1. This can be achieved by injecting the two flows of the slurry from the lines 2 and 13 (22 and 33) into the passage H1 through nozzles (not shown) co-currently in a direction tangential to the inside periphery of the cylindrical outer housing member H. The two nozzles connected to the lines 2 and 13 (22 and 33) are preferably angularly spaced apart from each other by 90-180 degrees. However, it is not necessary for the two nozzles to be located in the same horizontal plane.

Thus, the slurry introduced through the lines 2 and 13 (22 and 33) into lower parts of the outer passage H1 forms an ascending swirl therein and enters the inner passage P1 through the open topped end of the inside tubular member P. The slurry then flows down through the inner passage P1. The formation of the vortex gives the following advantages:

(1) The flows from the lines 2 and 13 (22 and 33) are homogeneously mixed effectively;
(2) Deflected flow of the slurry in the outer passage H1 is prevented so that the residence time of respective crystals in the outer passage H1 is uniform, ensuring uniform growth of the crystals; and
(3) The adduct crystals are prevented from precipitating and accumulating in the outer passage H1.

A portion of the slurry discharged from the bottom of the inner tubular member P of the first crystallization tower A is admixed with the cooled slurry which has been cooled in the cooler 26 and which is to be recycled to the second crystallization tower B. By such a direct heat exchange, the slurry from the first crystallization tower A can be effectively and efficiently cooled to permit the effective growth of large crystals.

The temperature of the raw material feed from the line 1 is generally higher by 1°-20° C. than the saturation temperature of the adduct. The crystallization in the tower A is performed at a temperature in the range of 45°-70° C. The slurry is cooled in the cooler 6 such that the slurry leaving the cooler 6 has a temperature lower by 10° C. or less, preferably by 5° C. or less, than that of the slurry prior to its passage through the cooler 6. The residence time of the phenol solution of BPA in the first crystallization tower A is generally 0.5-10 hours, preferably 0.5-5 hours. The slurry is heated in the heater 11 such that the slurry leaving the heater 11 has a temperature higher by 0.5°-5° C. than that of the slurry prior to its passage through the heater 11. The residence time of the slurry in the dissolution tank Q is generally 3-15 minutes. In the tank Q, crystals of the adduct having particle size of 100 μm or less are completely dissolved.

A further portion of the slurry discharged from the bottom of the inner tubular member P of the first crystallization tower A is passed through the line 7, the pump 8 and lines 9, 12 and 21 and is mixed with the cooled slurry from the cooler 26. The mixture is fed through the line 22 into a lower portion of the outer passage H1 of the second crystallization tower B. The slurry thus fed to the second crystallization tower B is treated in a manner similar to that of the first crystallization tower A to permit the crystals of the adduct to grow.

The crystallization in the tower B is performed at a temperature lower by generally 3°-10° C. than the crystallization temperature in the tank A. The slurry is heated in a heater 31 such that the slurry leaving the heater 31 has a temperature higher by 0.5°-5° C. than that of the slurry prior to its passage through the heater 31 so that the temperature within the tank Q is maintained at a temperature higher by 0.5°-5° C. than that of the crystallization tower B. In a dissolution tank Q connected to the second crystallization tower B, crystals of the adduct having particle size of 100 μm or less are completely dissolved. The concentration of the adduct in the slurry discharged from the bottom of the inner tubular member P1 of the second crystallization tower B is generally 35% by weight or less, preferably 25% by weight or less. The content of crystals of the adduct having a particle size of 100 μm or less is preferably controlled to not greater than 30% by weight, more preferably not greater than 20% by weight, based on the total weight of the adduct crystals.

A further portion of the slurry discharged from the second tower B is recovered as a product through a line 35. The slurry is then fed to a solid-liquid separator (not shown) to obtain high purity grown crystals of the adduct. The crystalline adduct is then decomposed to obtain BPA with a high purity and a good hue. If desired, the product slurry may be recovered by discharging a part of the heated slurry from the dissolution tank Q.

While the above-described second embodiment is composed of two crystallization zones A and B, it is possible to increase the number of the crystallization zones. Thus, the second embodiment generally uses two or more, first to n-th crystallization zones connected in series. The raw material feed is introduced into the first crystallization zone and the product slurry is recovered from the slurry in the downstream end, n-th crystallization zone. A portion of the slurry discharged from each of the first to (n−1)th crystallization zones is fed to the next crystallization zone located immediately downstream thereof. Another portion of the slurry is discharged from each of said first to n-th crystallization zones, introduced into its associated cooler and recycled back to the corresponding crystallization zone so that that the slurry in each of the first to n-th crystallization zones is cooled such that the temperature of the slurry in one crystallization zone is lower by generally 3°–10° C., preferably 5°–8° C., than that in the adjacent crystallization zone located upstream of the said one crystallization zone. The dissolution of fine crystals using the dissolution tank Q should be performed at least in the n-th crystallization tower. Namely, in part or all of the first to (n−1) th crystallization towers, such a dissolution step be omitted.

THIRD EMBODIMENT

Figure 3:
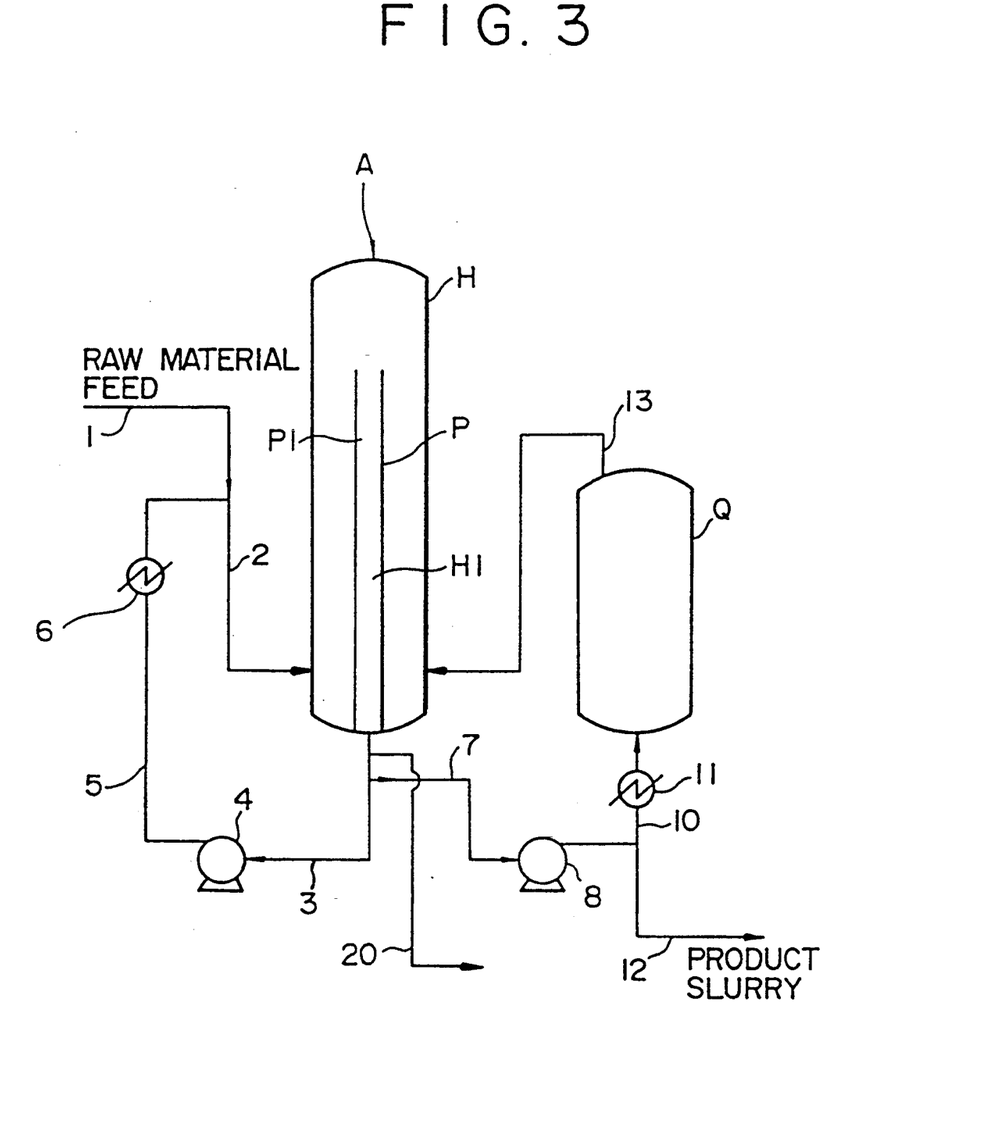

A further embodiment according to the present invention is illustrated in FIG. 3 in which the same reference numerals as in FIG. 1 designate similar component parts.

The apparatus shown in FIG. 3 has a crystallization tower A which is composed of an outer cylindrical housing H and an inner cylindrical member P defining therein an inner passage P1 and coaxially disposed within the outer housing H to define an outer passage H1 therebetween. The inner passage P1 is in fluid communication with the outer passage H1 only at an upper portion thereof. Designated as Q is a dissolution tank and as 6 is a cooler.

The crystallization tower A is not communicated with environmental atmosphere but is sealed with an inert gas to prevent the contact with oxygen. In this case, it is not necessary that the crystallization tower A have a highly pressure-resisting structure. When the inside of the tower A is communicated with the outside air, oxygen is apt to be adsorbed in a phenol solution contained in the tower A to cause the coloring of the adduct.

A raw material feed of a solution of BPA dissolved phenol is continuously introduced through lines 1 and 2 to a lower part of the outer passage H1 of the crystallization tower A and is directed upward through the outer passage H1. The solution is then allow to enter the inner passage P1 from the open topped end of the inside cylindrical member P and is directed downward therethrough. During the passage of the feed solution through the outer and inner passages H1 and P1 of the tower A, the solution is cooled to a predetermined temperature so that BPA is crystallized as an adduct of phenol to form a slurry containing seed crystals of the adduct.

For the purpose of effecting the cooling in the crystallization tower A, a portion of the slurry is discharged from the bottom of the inner cylindrical member P, introduced into a cooler 6 through a line 3, a pump 4 and a line 5 and then recycled to the tower A through the line 2.

Another portion of the slurry is discharged from the tower A, introduced into a dissolution vessel Q through a line 7, a pump 8, lines 9 and 10 and a heater 11, and then recycled to a lower portion of the outer passage H1 of the crystallization tower A through a line 13. By this, fine crystals contained in the discharged slurry are dissolved and, hence, the proportion of large crystals of the adduct contained in the slurry within the tower A is increased. Fine crystals of the adduct formed in the tower A have a large surface area and are apt to adsorb impurities which account for the coloring of the adduct. By the decrease of the amount of such fine crystals, therefore, it is possible to obtain seed crystals with good hue. Preferably, the content of crystals of the adduct having a particle size of 100 μm or less is adjusted to not greater than 30% by weight, more preferably not greater than 20% by weight, based on the total weight of the adduct crystals recovered from the first crystallization tower A.

A further portion of the slurry is discharged from the bottom of the tower A through a line 20 for recovery. The line 20 is used when the recovered slurry is able to be fed to a next step by gravity. When such a gravity flow is not feasible, the product slurry is recovered through a line 12 by operation of the pump 8. Alternatively, the product slurry may also be recovered through a line (not shown) branched from the line 13. The product slurry may be fed to a solid-liquid separator (not shown) to obtain high purity grown crystals of the adduct. The crystalline adduct is then decomposed to obtain BPA with a high purity and a good hue. Alternatively, the product slurry may be introduced as such or after removal of the mother liquor into a crystallization zone to grow the crystals of the adduct.

In this embodiment, the slurry from the lines 2 and 13 is introduced into the tower A in such a manner that an upwardly flowing vortex is established in the outer passage H1. This can be achieved by injecting the two flows of the slurry from the lines 2 and 13 into the passage H1 through nozzles (not shown) co-currently in a direction tangential to the inside periphery of the cylindrical outer housing member H. The two nozzles connected to the lines 2 and 13 are preferably angularly spaced apart from each other by 90–180 degrees for reasons of establishing smooth vortex flow. However, it is not necessary for the two nozzles to be located in the same horizontal plane.

Thus, the slurry introduced through the lines 2 and 13 into lower parts of the outer passage H1 forms an ascending swirl therein and enters the inner passage P1 through the open topped end of the inside tubular member P. The slurry then flows down through the inner passage P1. The formation of the vortex in the outer passage H1 gives the following advantages:

(1) The flows from the lines 2 and 13 are homogeneously mixed effectively;
(2) Deflected flow of the slurry in the outer passage H1 is prevented so that the residence time of respective crystals in the outer passage H1 is uniform, ensuring uniform growth of the crystals; and
(3) The adduct crystals are prevented from precipitating and accumulating in the outer passage H1.

The temperature of the raw material feed supplied through the line 1 is generally higher by 1°–20° C. than the saturation temperature of the adduct. The crystallization in the tower A is performed at a temperature in the range of 45°–70° C. The slurry is cooled in the cooler 6 such that the slurry leaving the cooler 6 has a temperature lower by 10° C. or less, preferably by 5° C. or less, than that of the slurry prior to its passage through the cooler 6. The residence time of the phenol solution of BPA in the first crystallization tower A is generally 0.5–10 hours, preferably 0.5–5 hours. The slurry is heated in the heater 11 such that the slurry leaving the heater 11 has a temperature higher by 0.5°–5° C. than that of the slurry prior to its passage through tile heater 11. The residence time of the slurry in the dissolution tank Q is generally 3–15 minutes. In the tank Q, crystals of the adduct having particle size of 100 μ m or less are completely dissolved.

FOURTH EMBODIMENT

Figure 4:
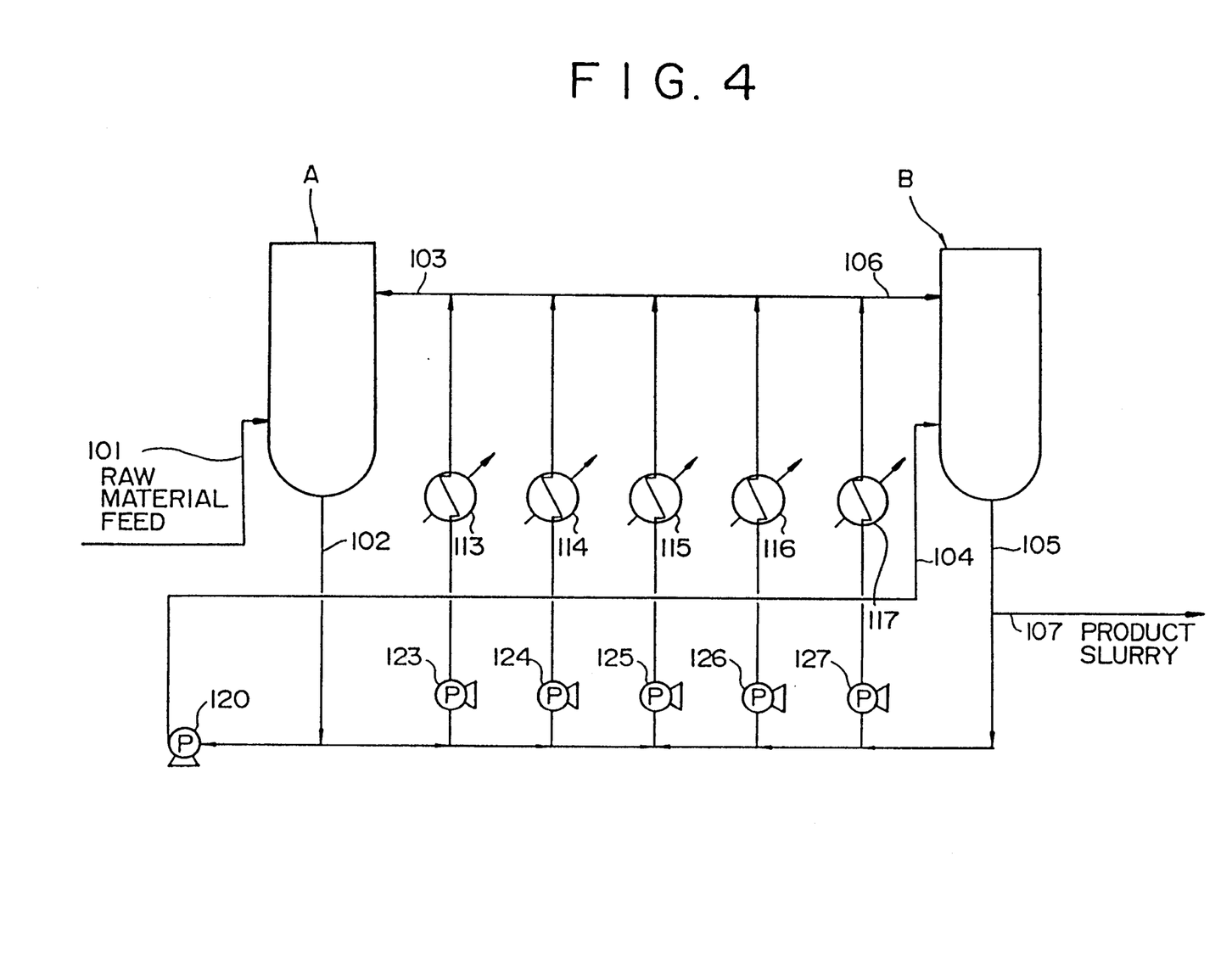

FIG. 4 illustrates an apparatus suitable for carrying out a fourth embodiment of the process according to the present invention.

The apparatus shown in FIG. 4 has two, first and second crystallization towers A and B which are connected in series by lines 102 and 104. The reference numerals 113 and 114 denote coolers associated with the first crystallization tower A while the reference numerals 116 and 117 denote coolers associated with the second crystallization tower B. Designated as 115 is a common cooler which is used as a substitute for one of the coolers 113, 114, 116 and 117.

A raw material feed of a solution of BPA dissolved in phenol is continuously introduced through a line 101 to a lower part of the first crystallization tower A where the feed solution is cooled to a predetermined temperature so that BPA is crystallized as an adduct of phenol to form a slurry containing seed crystals of the adduct. Part of the slurry is discharged from the tower A through tile line 102 and a portion of the discharged slurry is fed through a pump 120 and tile line 104 to the second crystallization tower B. In the tower B, the slurry is further cooled so that the crystals of the adduct grow. Part of the slurry is discharged from the tower B through a line 105 and a portion of the discharged slurry is recovered through a line 107. The slurry product thus recovered is introduced into a solid-liquid separator to obtain the adduct crystals.

For the purpose of effecting the cooling in the first and second crystallization towers A and B, portions of the slurry discharged from the towers A and B are introduced into selected two of the coolers 113–117 and recycled to the towers A and B through lines 103 and 106, respectively.

More particularly, a portion of the slurry discharged from the first crystallization tower A is fed to selected two of the coolers 113–115 by operation of selected two of pumps 123–125 and recycled to the tower A through the line 103. The temperature within the tower A depends upon the temperatures and feed rates of the liquids introduced through the lines 101 and 103. The crystallization of the adduct proceeds until the saturation concentration at that temperature within the tower A is reached. Similarly, a portion of the slurry discharged from the second crystallization tower B is fed to selected two of the coolers 115–117 by operation of selected two of pumps 125–127 and recycled to the tower B through the line 106. The temperature within the tower B depends upon the temperatures and feed rates of the liquids introduced through the lines 104 and 106. The crystallization of the adduct proceeds until the saturation concentration at that temperature within the tower B is reached.

Means including valves are provided and periodically switched so that selected four of the coolers 113–117 are used for the cooling of the towers A and B, with the remaining cooler being subjected to a cleaning treatment. An example of the sequence of the operation of the coolers 113–117 is given in Table 1 below.

TABLE 1

| Operation Mode | Mode 1 | Mode 2 | Mode 3 | Mode 4 | Mode 5 |
| --- | --- | --- | --- | --- | --- |
| Cooler 113 | A | — | A | A | A |
| Cooler 114 | A | A | A | — | A |
| Cooler 115 | — | A | B | A | B |
| Cooler 116 | B | B | — | B | B |
| Cooler 117 | B | B | B | B | — |

In Table 1, the letter "A" indicates that the cooler is used for cooling the first crystallization tower while the letter "B" indicates that the cooler is used for cooling the second crystallization tower B. The symbol "-" indicates that the cooler is not used for cooling the tower A or B but is subjected to a cleaning treatment. For instance, in Mode 5, the cooling of the first crystallization tower A is performed with the coolers 113 and 114 while the second crystallization tower B is cooled with the coolers 115 and 116, with the cooler 117 being subjected to cleaning of the heat-exchange surface. After the termination of a predetermined period of time through which the operation in Mode 5 has been continued, the control means are operated so that the process is switched to Mode 1.

The cleaning of the cooler is performed for removing deposits of crystalline adduct from the cooling (heat-exchange) surface thereof. This can be suitably effected by introducing a heating medium into the cooler to heat and fuse the deposits on the heat-exchange surface. Since the period of time required for regenerating one cooler is much shorter than the period of time through which a regenerated cooler remain operable, the above cycle shown in Table 1 can work without difficulty.

Thus, in the fourth embodiment, two or more cooling zones connected in parallel with each other are provided for one crystallization zone. A portion of the slurry discharged from the crystallization zone is fed to all of the associated cooling zones except one cooling zone whose cooling surface bears deposits of crystals of the adduct to cool the slurry introduced thereinto with the simultaneous formation of crystals of the adduct part of which deposits on the cooling surfaces thereof. The one cooling zone is treated for removing the deposits from the cooling surface thereof during the cooling of the tower with the all but one cooling zones.

In the above-described embodiment, the line including the cooler 115 and the pump 125 is commonly used for the cooling of the first or second crystallization towers A and B while the coolers 113 and 114 and coolers 116 and 117 are exclusively used for the first and second crystallization towers A and B, respectively. However, if desired, respective coolers 113–117 may be commonly used for the towers A and B.

While the process of the fourth embodiment can be performed with only one crystallization tower, it is preferred that two crystallization towers be used as illustrated in FIG. 4 for reasons of obtaining large crystals of the adduct having an improved purity. Namely, by using two towers connected in series, it is possible to make the difference in temperature between the inside of each of the towers and the BPA/phenol feed so that rapid crystallization of the adduct can be avoided, enabling the formation of large adduct crystals with a high purity. Additionally, the use of two towers permits the lowering of the load of the coolers so that the deposition of the adduct on the heat-exchange surfaces of the coolers can be reduced.

In each of the coolers, the slurry containing crystals of the adduct is cooled by indirect heat exchange with a cooling medium. Crystals are formed after the liquid phase of the slurry has become in a supersaturated state. Since seed crystals are already present, the growth of the crystals predominantly proceeds in the coolers rather than the formation of new crystal seeds. As the process proceeds, however, scales composed of fine crystals of the adduct and impurities begin depositing on the heat-exchange surfaces. Once the deposits are formed, crystallization proceed acceleratingly with the deposits serving as seeds of crystals and the heat-exchange efficiency of the cooler is rapidly deteriorated to the extent that the cooling failure occurs. Further, part of the deposits is occasionally spontaneously removed from the heat-exchange surface and the resulting scales contaminate the slurry in the crystallization towers to cause the reduction of the purity of the product. Thus, it becomes necessary to clean such a cooler for the removal of scales. Conventionally, the cleaning of the cooler has been performed by removing the cooler from the process line after stop page of the process.

According to the process of the present invention, the above problems have been satisfactorily solved. When scales begin forming on tile heat-exchange surface of a cooler, the feed of the slurry to the cooler is shifted to another fresh cooler and a heating medium is fed to the fouled cooler to fuse and remove the scale before the growth thereof. Accordingly, it is not necessary to stop the process. Further, the regeneration of the cooler can be easily effected.

FIFTH EMBODIMENT

Figure 5:
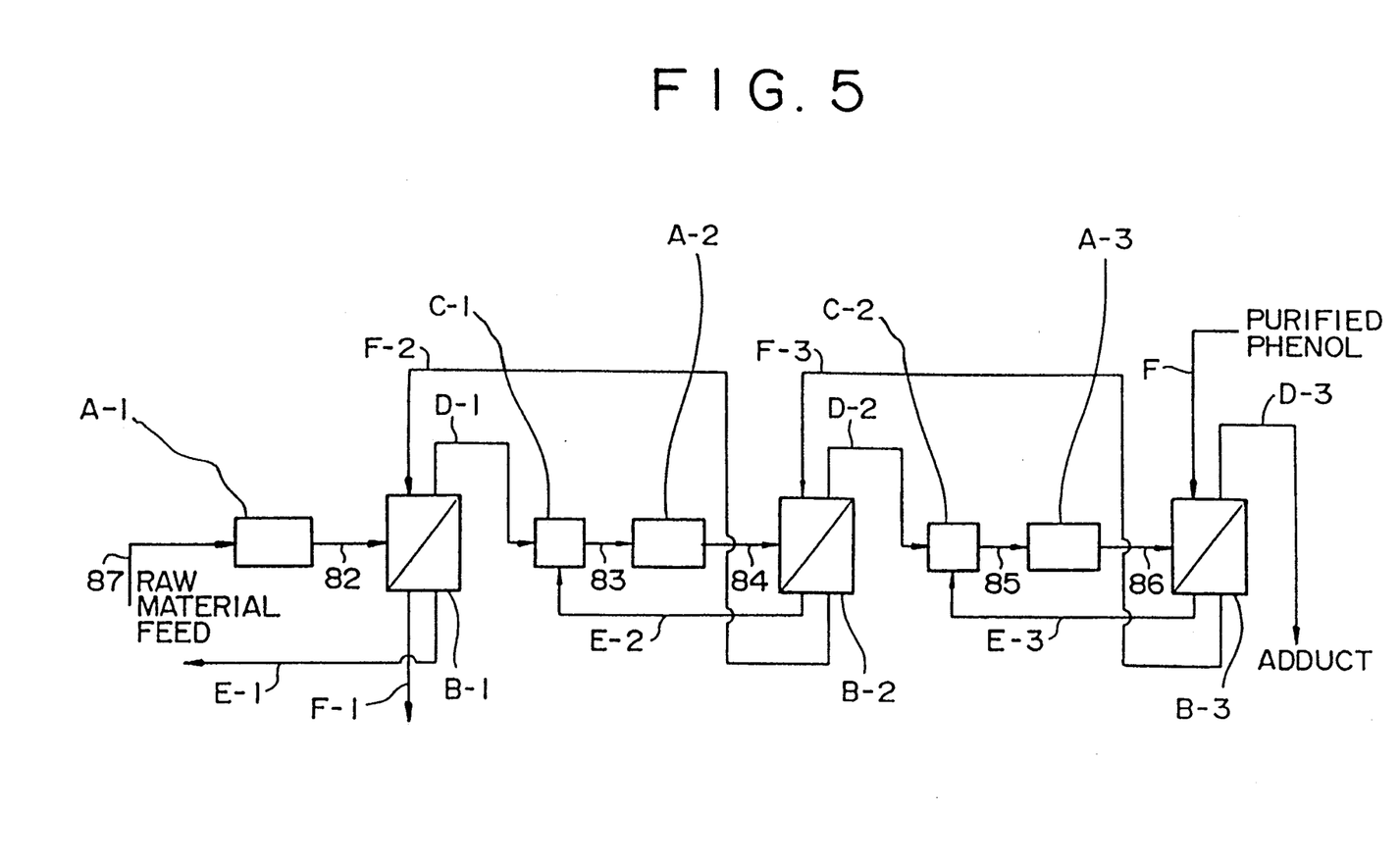

FIG. 5 illustrates a fifth embodiment of the process according to the present invention. Designated as A-1 through A-3 are first through third crystallization zones, respectively, as B-1 through B-3 are first through third solid/liquid separation zones, respectively, and as C-1 and C-2 are first and second dissolution zones, respectively.

A raw material solution of BPA dissolved in phenol is fed through a line 87 to the first crystallization zone A-1 where the solution is cooled to crystallize an adduct of BPA and phenol and to obtain a first slurry containing crystals of the adduct. The first slurry is discharged from the first crystallization zone A-1 and is introduced through a line 82 into the first solid-liquid separating zone B-1 where the slurry is separated into a first solid phase containing crystals of the adduct and a first liquid phase containing phenol. The first liquid phase is discharged from the separating zone B-1 through a line F-1 and is introduced, optionally after being treated for the reduction of the amount of impurities, into a reaction zone (not shown) in which acetone is reacted with phenol to form BPA. The first solid phase is washed with a second liquid phase, described hereinafter, and the waste washing liquid is fed through a line E-1 to the reaction zone.

The first solid phase thus washed is fed through a line D-1 to the first dissolution zone C-1 where it is dissolved in a waste washing liquid supplied from the second solid-liquid separation zone B-2 through a line E-2 to obtain a second solution. The second solution is fed through a line 83 to the second crystallization zone A-2 where the second solution is cooled to crystallize an adduct of BPA and phenol and to obtain a second slurry containing crystals of the adduct. The second slurry is discharged from the second crystallization zone A-2 and is introduced through a line 84 into the second solid-liquid separating zone B-2 where the slurry is separated into a second solid phase containing crystals of the adduct and a second liquid phase containing phenol. The second liquid phase is discharged from the separating zone B-2 and is introduced through a line F-2 into the first solid-liquid separation zone B-1 for washing the first solid phase as described previously. The second solid phase is washed with a third liquid phase, described hereinafter, and the waste washing liquid is fed through the line E-2 to the first dissolution zone C-1 and is used for dissolving the first solid phase, as described previously.

The second solid phase thus washed is fed through a line D-2 to the second dissolution zone C-2 where it is dissolved in a waste washing liquid supplied from the third solid-liquid separation zone B-3 to obtain a third solution. The third solution is fed through a line 85 to the third crystallization zone A-3 where the solution is cooled to crystallize an adduct of BPA and phenol and to obtain a third slurry containing crystals of the adduct. The third slurry is discharged from the third crystallization zone A-3 and is introduced through a line 86 into the third solid-liquid separating zone B-3 where the slurry is separated into a third solid phase containing crystals of the adduct and a third liquid phase containing phenol. The third liquid phase is discharged from the separating zone B-3 and is introduced through the line F-3 into the second solid-liquid separation zone B-2 for washing the second solid phase as described previously. The third solid phase is washed with purified phenol, described hereinafter, and the waste washing liquid is fed through a line E-3 to the second dissolution zone C-2 to dissolve the second solid phase as described previously.

The third solid phase thus washed is recovered through a line D-3 as product. As the phenol to be used for washing the third solid phase, phenol having APHA color of 15 or less may be used. Preferably, the purified phenol described previously in connection with the first embodiment is used.

The above fifth embodiment specifically shown in FIG. 5 uses three crystallization zones. But the number of the crystallization zones is not limited to only three but can be "n" which is two or more. In this case, the liquid phase obtained in one solid-liquid separation zone is used as at least part of the washing liquid for washing the solid phase obtained in the stage which immediately precedes the one separation zone. If desired, a part of the waste washing liquid obtained in the one separation zone may be used in conjunction with the liquid phase of the one separation zone for washing the solid phase of the immediately preceding separation zone. Further, the waste washing liquid obtained in one solid-liquid separation zone is used as at least part of the solvent for dissolving the solid phase obtained in the stage which immediately precedes the one separation zone. If desired, a part of the liquid phase obtained in the one separation zone may be used in conjunction with the waste washing liquid of the one separation zone for dissolving the solid phase of the immediately preceding separation zone.

In the fifth embodiment, the purity of the solvent phenol to be used for dissolving the solid phase obtained in one solid-liquid separation zone is higher than the solvent used for dissolving the solid phase obtained in the adjacent separation zone located upstream of the one separation zone. Further, the purity of the washing liquid to be used for washing the solid phase obtained in one solid-liquid separation zone is higher than the washing liquid used for washing the solid phase obtained in the adjacent separation zone located upstream of the one separation zone. Therefore, the content of impurities in the slurry in one crystallization zone is smaller than that in the slurry of any upstream crystallization zone. The term "impurities" used immediately above is intended to refer to by-products produced during the reaction of phenol with acetone and include, for example, isomers of BPA, chroman and derivatives thereof.

In the above-described embodiment, some or all of the washing steps of the first through (n−1)th solid-liquid separation zones may be omitted, if desired. In this case, the liquid phase obtained in the separation zone in which no washing is performed is used as at least part of the solvent phenol for dissolving the solid phase in the preceding separation zone. By controlling the amounts of the washing liquids to be used in respective solid-liquid separation zones, the overall amount of phenol to be used in the process can be reduced to lower the operation costs.

The fifth embodiment in which the adduct is subjected to repeated recrystallization uses purified phenol in the downstream end, n-th stage only. Nonetheless, the product crystalline adduct has a high purity.

SIXTH EMBODIMENT

In this embodiment, a raw material feed which is a solution of BPA in phenol is cooled to obtain a slurry containing an adduct of BPA and phenol. As the raw material feed, there may be used a product obtained by reaction of phenol with acetone or a solution obtained by dissolving the adduct of BPA and phenol in phenol.

The slurry is filtered to separate same into the adduct crystals and a mother liquor. The filtration is performed under such conditions that at least part of the adduct crystals having a particle diameter of 100 μm or less are passed to the mother liquor (filtrate) and that the content of crystals having a particle diameter of 100 μm or less in the adduct crystals separated is 20% by weight or less, preferably 15% by weight of less. Such filtration conditions can be established by using an adequate filter and/or by adopting specific filtration procedures. A filter having openings with a diameter of 100–150 μm, preferably 100–125 μm, is suitably used. The control of the thickness of the cake of crystals on the filter and the number of backwash operations of the cake can also be effective in controlling the particle size of the adduct crystals.

The thus obtained crystals are preferably washed with purified phenol to improve the purity thereof. such purified phenol may be one described with reference to the first embodiment. The washing may be performed by feeding purified phenol to the solid-liquid separator in which the adduct crystals have been separated or by feeding the adduct crystals to a washing vessel. The purified phenol is used in an amount of at least 50 parts by weight, preferably at least 100 parts by weight, per 100 parts by weight of the adduct crystals to be washed. The washed adduct is thermally stable and scarcely colored.

The washed crystals are then fed to a separation zone for separating phenol from the crystals and to recover BPA. The separation can be effected in any known manner such as by distillation, extraction or steam stripping. The BPA thus recovered also has a high quality and is scarcely colored.

The following examples will further illustrate the present invention. "Percentages" are by weight. The APHA number referred to in the examples is measured in accordance with the method specified in ASTM D 1686, "Standard Test Method for color of Solid Aromatic Hydrocarbons and Related Materials in the Molten State".

EXAMPLE 1

Second Embodiment

A raw material feed having the composition shown below was subjected to crystallization using the apparatus shown in FIG. 2. The slurry recovered through the line 35 was treated for the separation of crystals of BPA/phenol adduct. The thus obtained adduct had APHA color of 15 and contained 13% of fine crystals with a particle diameter of 100 μm or less. The operation conditions of the first and second crystallization towers A and B and in the associated dissolution tanks Q thereof are shown below.

Raw material feed of line 1:
BPA: 22%
Phenol: 74%
Others: 4%
First crystallization tower A:
Temperature: 54° C.
Residence time: 120 minutes
Dissolution tank Q of tower A:
Temperature: 55° C.
Residence time: 6 minutes
Second crystallization tower A:
Temperature: 47° C.
Residence time: 120 minutes
Dissolution tank Q of tower B:
Temperature: 48° C.
Residence time: 6 minutes Comparative Example 1

Example 1 was repeated in the same manner as described except that the second crystallization tower and the associated cooler and dissolution tank were omitted and that the operation temperatures in the crystallization tower A and the tank Q were 47° C. and 48° C., respectively. The slurry recovered through the line 12 was treated for the separation of crystals of BPA/- phenol adduct. The thus obtained adduct had APHA color of 30 and contained 29% of fine crystals with a particle diameter of 100 μm or less.

Example 2

Third Embodiment

A raw material feed having the composition shown below was subjected to crystallization using the apparatus shown in FIG. 3. The slurry recovered through the line 20 was treated for the separation of crystals of BPA/phenol adduct. The thus obtained adduct contained 20% of fine crystals with a particle diameter of 100 μm or less. The operation conditions of the crystallization tower A and in the associated dissolution tank Q thereof are shown below.

Raw material feed of line 1:
BPA: 22%
Phenol: 74%
Others: 4%
Cystallization tower A:
Temperature: 54° C.
Residence time: 120 minutes
Dissolution tank Q:
Temperature: 55° C.
Residence time: 6 minutes

EXAMPLE 3

Third Embodiment

A raw material feed having the composition shown below was subjected to crystallization using the apparatus shown in FIG. 3. The slurry recovered through the line 20 was treated for the separation of crystals of BPA/phenol adduct. The thus obtained adduct contained 29.5% of fine crystals with a particle diameter of 100 μm or less. The operation conditions of the crystallization tower A and in the associated dissolution tank Q thereof are shown below.

Raw material feed of line 1:
BPA: 22%
Phenol: 74%
others: 4%
Crystallization tower A:
Temperature: 44° C.
Residence time: 120 minutes
Dissolution tank Q:
Temperature: 49° C.
Residence time: 4 minutes

Comparative Example 2

Example 3 was repeated in the same manner as described except that the dissolution step was omitted. Namely, in this example, the recirculating line including the line 7, pump 8, line 10, heater 11, tank Q and line 13 was closed throughout the process. As a result, the crystals of BPA/phenol adduct recovered from the slurry from the line 20 contained 69% of fine crystals with a particle diameter of 100 μm or less.

Reference Example of Example 4

Raw material phenol (water content: 0.1%) was contacted with a sulfonic acid-type cation exchange resin (Amberlite IR-118H+, manufactured by Rohm & Haas Company) at 80° C. for 50 minutes. The thus treated phenol was then distilled at a distillation tower bottom temperature of 175° C., a tower top pressure of 560 Torr to obtain purified phenol whose APHA color was 5.

Acetone was reacted with phenol in the presence of an acid catalyst to obtain a mixture containing BPA and phenol. The mixture was then cooled to 50° C. to obtain 3000 g of a first slurry containing 20% of a crystalline adduct of BPA and phenol. The first slurry was suction filtered at 50° C. to obtain a first solid phase and 2250 g of a first mother liquor (A-ML). The first solid phase was washed with 600 g of the above purified phenol to obtain a first washed adduct and 580 g of a first waste washing liquid (B-WW).

The first washed adduct was dissolved into 1310 g of the above purified phenol and recrystallized at 50° C. to obtain a second slurry containing 20% of a crystalline adduct of BPA and phenol. The second slurry was suction filtered at 50° C. to obtain a second solid phase and 1430 g of a second mother liquor (C-ML). The second solid phase was wasted with 600 g of the above purified phenol to obtain a second washed adduct and 580 g of a second waste washing liquid (D-WW). The second washed adduct was again washed with 600 g of the above purified phenol to obtain a third washed adduct and 580 g of a third waste washing liquid (E-WW). The third washed adduct was found to have APHA color of 5 and an impurity content of 100 ppm by weight.

EXAMPLE 4

Fifth Embodiment

Acetone was reacted with phenol in the presence of an acid catalyst to obtain a mixture containing BPA and phenol. The mixture was then cooled to 50° C. to obtain 3000 g of a first slurry containing 20% of a crystalline adduct of BPA and phenol. The first slurry was suction filtered at 50° C. to obtain a first solid phase and a first mother liquor. The first solid phase was washed with 700 g of C-ML obtained in the above Reference Example to obtain a first washed adduct and a first waste washing liquid.

The first washed adduct was dissolved into a mixture of 730 g of C-ML and 580 g of D-WW, both of which were obtained in the above Reference Example, and recrystallized at 50° C. to obtain a second slurry containing 20% of a crystalline adduct of BPA and phenol. The second slurry was suction filtered at 50° C. to obtain a second solid phase and a second mother liquor. The second solid phase was washed with 580 g of E-WW obtained in the above Reference Example to obtain a second washed adduct and a second waste washing liquid. The second washed adduct was again washed with 600 g of the purified phenol obtained in the above Reference Example to obtain a third washed adduct and a third waste washing liquid. The third washed adduct was found to have APHA color of 5 and an impurity content of 100 ppm by weight.

From the results of Example 4 and Reference Example, it is appreciated that the product obtained in Example 4 has the same quality as that in Reference Example in spite of the fact that, in Example 4, purified phenol is used only in the final washing step.

EXAMPLE 5

Sixth Embodiment

Acetone was reacted with phenol in the presence of an acid catalyst to obtain a mixture containing BPA and phenol. The mixture was then cooled to 50° C. to obtain of a slurry containing 20% of a crystalline adduct of BPA and phenol. The slurry was suction filtered at 50° C. using a filter having a mesh size of 106 μm to separate crystals of adduct. The adduct crystals thus separated were washed with purified phenol to obtain a washed product. This product was found to have APHA color of 10 and an impurity content of 100 ppm by weight and to contain 5% of fine crystals with a particle diameter of 100 μm or less.

The above procedure was repeated in the same manner as described using various filters having different mesh sizes, thereby obtaining crystalline adduct products. The content of fine crystals with a particle diameter of 100 μm or less, the APHA color and the content of impurity (chroman compounds) of each of the products are summarized in Table 2 below.

TABLE 2

| Experiment No. | Content of Fine Crystals (%) | APHA Color | Impurity Content (wt ppm) |
|---|---|---|---|
| 1 | 5 | 10 | 100 |
| 2 | 10 | 15 | 110 |
| 3 | 20 | 20 | 150 |
| 4 | 35 | 30 | 230 |
| 5 | 40 | 40 | 400 |

From the results shown in Table 2, it is appreciated that crystalline adduct having a content of fine crystals with a particle diameter of 100 μm or less of 20% by weight or less has a good color and a low impurity content.

What is claimed is:

1. A crystallization device, comprising:

a first crystallization tower for containing a slurry of crystals of an adduct of bisphenol A and phenol dispersed in phenol and having a recycling port, a discharge port and a feed port;

a feed conduit connected to said feed port of said first crystallization tower for feeding a liquid mixture of bisphenol A and phenol;

a second crystallization tower containing a slurry of crystals of an adduct of bisphenol A and phenol dispersed in phenol and having a recycling port, a discharge port and a feed port;

a first group of two or more coolers each having inlet and outlet ports;

a second group of two or more coolers each having inlet and outlet ports;

a common cooler having inlet and outlet ports;

feed conduit means extending between said discharge port of said first crystallization tower and the feed port of said second crystallization tower and having feed pump means for feeding a portion of the slurry in said first crystallization tower into said second crystallization tower through said feed conduit means;

first introduction conduit means extending between said discharge port of said first crystallization tower and the inlet port of each of said coolers of said first group;

first recycling conduit means extending between said recycling port of said first crystallization tower and the outlet port of each of said coolers of said first group;

second introduction conduit means extending between said discharge port of said second crystallization tower and the inlet port of each of said coolers of said second group;

second recycling conduit means extending between said recycling port of said second crystallization tower and the outlet port of each of said coolers of said second group;

a recovery conduit in communication with said discharge port of said second crystallization port for discharging part of the slurry from said second crystallization tower therethrough for recovery;

common introduction conduit means for communicating the inlet port of said common cooler with the discharge port of each of said first and second crystallization towers;

common recycling conduit means for communicating the outlet port of said common cooler with the recycling port of each of said first and second crystallization towers;

first pump means operable to continuously discharge part of the slurry from said first crystallization tower, to pass the discharged slurry through said first group of coolers and to return the discharged slurry after the passage of said coolers to said recycling port of said first crystallization tower;

second pump means operable to continuously discharge part of the slurry from said second crystallization tower, to pass the discharged slurry through said second group of coolers and to return the discharged slurry after the passage of said coolers to said recycling port of said second crystallization tower;

third pump means operable to continuously discharge part of the slurry from said first or second crystallization tower, to pass the discharged slurry through said common cooler and to return the discharged slurry after the passage of said common cooler to said recycling port of said first or second crystallization tower; and controlling means to control the operations of said first, second and third pump means so that selected one of said common cooler and first and second groups of cooler is prevented from being fed with the discharged slurry, whereby the slurry within each of said first and second crystallization towers is cooled with the recycled slurry which has been passed through the said coolers to cause the crystals in each of said first and second crystallization towers to grow.

* * * * *